(12) United States Patent
Lastow et al.

(10) Patent No.: US 11,058,832 B2
(45) Date of Patent: Jul. 13, 2021

(54) SINGLE DOSE DRY POWDER INHALER

(71) Applicant: Iconovo AB, Lund (SE)

(72) Inventors: Orest Lastow, Torna Haellestad (SE); Lars Arvidsson, Dalby (SE)

(73) Assignee: ICONOVO AB

( * ) Notice: Subject to any disclaimer, the term of this patent is extended or adjusted under 35 U.S.C. 154(b) by 261 days.

(21) Appl. No.: 15/579,067

(22) PCT Filed: Jun. 2, 2016

(86) PCT No.: PCT/EP2016/062511
§ 371 (c)(1),
(2) Date: Dec. 1, 2017

(87) PCT Pub. No.: WO2016/193379
PCT Pub. Date: Dec. 8, 2016

(65) Prior Publication Data
US 2018/0169354 A1    Jun. 21, 2018

(30) Foreign Application Priority Data

Jun. 3, 2015 (SE) .................................. 1550711-4

(51) Int. Cl.
*A61M 15/00* (2006.01)
(52) U.S. Cl.
CPC ........ *A61M 15/0028* (2013.01); *A61M 15/00* (2013.01); *A61M 2202/064* (2013.01)
(58) Field of Classification Search
CPC .......... A61M 15/0028; A61M 15/0031; A61M 15/003; A61M 15/0043; A61M 15/0045;
(Continued)

(56) References Cited

U.S. PATENT DOCUMENTS 5,772,961 A * 6/1998 Mico ..................... B01L 3/5023
422/412
5,911,937 A * 6/1999 Hekal .................. B65D 81/266
264/255
(Continued)

FOREIGN PATENT DOCUMENTS

DE   102009041664 A1 * 3/2011 ........ A61M 15/0028
WO   WO-9613291 A1     5/1996
(Continued)

OTHER PUBLICATIONS

English Machine Translation of DE-102009041664 powered by European Patent Office, Accessed Oct. 18, 2019 (Year: 2011).*

*Primary Examiner* — Kendra D Carter
*Assistant Examiner* — Brian T Khong
(74) *Attorney, Agent, or Firm* — Fishman Stewart PLLC (57) ABSTRACT

A dry powder inhaler may include a housing having a lower housing part defining at least one air inlet and at least one air outlet. At least one container may be disposed in the lower housing part. The at least one container may include a cavity for a dry powder drug. A chamber may be disposed above the at least one container for deaggregation of the dry powder drug after emptying of the dry powder drug from the cavity. Upon inhalation by a user at the at least one air outlet, air may flow from the at least one air inlet into and through the chamber to empty the dry powder drug from the cavity and convey the dry powder drug to the at least one outlet.

18 Claims, 13 Drawing Sheets

(58) Field of Classification Search
CPC .......... A61M 15/0046; A61M 15/0048; A61M 15/006; A61M 15/0006; A61M 15/0061; A61M 15/0063; A61M 2202/064; A61M 15/0005; A61M 15/0008
See application file for complete search history.

(56) References Cited

U.S. PATENT DOCUMENTS

| | | | | |
|---|---|---|---|---|
| 6,214,255 | B1* | 4/2001 | Hekal | B01J 20/28042 252/194 |
| 6,221,446 | B1* | 4/2001 | Hekal | B01J 20/28014 206/204 |
| 7,533,668 | B1* | 5/2009 | Widerstrom | A61M 15/0028 128/203.12 |
| 9,283,337 | B2 | 3/2016 | Lastow et al. | |
| 2002/0092523 | A1* | 7/2002 | Connelly | A61M 15/0028 128/203.15 |
| 2003/0180228 | A1* | 9/2003 | Cripps | B65D 81/266 424/46 |
| 2004/0182387 | A1* | 9/2004 | Steiner | A61M 16/0825 128/203.15 |
| 2005/0268911 | A1* | 12/2005 | Cross | A61M 15/0045 128/204.17 |
| 2007/0202538 | A1* | 8/2007 | Glezer | B01L 3/5085 435/7.1 |
| 2007/0277821 | A1* | 12/2007 | Oliva | A61M 15/0028 128/203.15 |
| 2008/0012172 | A1* | 1/2008 | Merical | B32B 27/18 264/254 |
| 2008/0190424 | A1* | 8/2008 | Lucking | A61K 9/0075 128/203.15 |
| 2008/0268023 | A1* | 10/2008 | Palmer | A61K 9/006 424/435 |
| 2009/0057189 | A1* | 3/2009 | Silvenis | A61J 1/035 206/570 |
| 2009/0205656 | A1* | 8/2009 | Nishibayashi | A61M 15/0065 128/203.15 |
| 2009/0250058 | A1* | 10/2009 | Lastow | A61M 15/0028 128/203.15 |
| 2009/0308390 | A1* | 12/2009 | Smutney | A61K 47/22 128/203.15 |
| 2010/0024814 | A1* | 2/2010 | Sugita | A61M 15/0021 128/203.14 |
| 2010/0154795 | A1* | 6/2010 | Pentafragas | A61M 15/0043 128/203.15 |
| 2011/0083667 | A1* | 4/2011 | Briant | A61M 15/0045 128/203.15 |
| 2012/0145150 | A1* | 6/2012 | Donovan | A61M 15/0028 128/203.15 |
| 2013/0104887 | A1* | 5/2013 | Smutney | A61M 15/0028 128/203.15 |
| 2013/0256331 | A1* | 10/2013 | Giraud | A61J 7/0418 221/1 |
| 2014/0158126 | A1* | 6/2014 | Parry-Billings | A61M 15/0026 128/203.15 |
| 2018/0169354 | A1 | 6/2018 | Lastow et al. | |

FOREIGN PATENT DOCUMENTS

| | | | |
|---|---|---|---|
| WO | WO-2008008021 | A1 | 1/2008 |
| WO | WO-2009082341 | A1 | 7/2009 |
| WO | WO-2009082343 | A1 | 7/2009 |
| WO | WO-2010021589 | A1 * | 2/2010 ........ A61M 15/0051 |
| WO | WO-201024759 | A1 | 3/2010 |
| WO | WO-2014/048895 | A1 | 4/2014 |
| WO | WO-2015097034 | A1 * | 7/2015 |

* cited by examiner

SINGLE DOSE DRY POWDER INHALER

CROSS-REFERENCE TO RELATED APPLICATIONS

This application claims priority to International Application PCT/EP2016/062511 filed on Jun. 2, 2016, and to Swedish Application SE 1550711-4 filed on Jun. 3, 2015, the contents of each of which are hereby incorporated by reference in their entirety.

TECHNICAL FIELD

This invention pertains in general to the field of medicament inhalers, and more particularly to dry powder inhalers for one dose administration.

BACKGROUND

Inhalers have been widely used in the pharmaceutical field for treatment of respiratory and/or other diseases. Numerous drugs, medications and other substances are inhaled into the lungs using the inhalers for rapid absorption of the drug etc. in the blood stream and for local action in the lung.

Inhaled drugs fall into two main categories, one being in the form of liquids, including suspensions, and the other being powders. The choice of liquids or powders depends on the characteristics of the drugs, medications, etc. to be inhaled.

The most common type of inhaler is the pressurized metered-dose inhaler. In this type of inhaler medication is most commonly stored in solution in a pressurized canister that contains a propellant, although it may also be a suspension. The canister is attached to a plastic, hand-operated actuator. On activation, the metered-dose inhaler releases a fixed dose of medication in aerosol form.

Another kind of inhaler is a nebulizer, which supplies medication as an aerosol created from an aqueous formulation.

The kind referred to herein is yet another type in the form of a dry powder inhaler, and specifically a one dose dry powder inhaler. A dry powder inhaler releases a metered or device-metered dose of powdered medication that is inhaled through the inhaler.

Dry powder inhalers need to deliver a particle size that is predominantly below 5 microns, and preferably between 1 micron and 3.3 microns, for maximum effectiveness. However, such small particles are very cohesive due to high surface energy. As cohesiveness may be worsened by moisture, it is appropriate to keep the metered dose of drug/medication protected from moisture in a container that is opened shortly before inhalation in order that the drug/medication may exit the container. Agglomeration of small particles is a problem which results in the active particles leaving the inhaler as large agglomerates.

WO2008008021 relates to an inhalation system for the administration of a drug in the form of dry powder by inhalation through an airflow path. The system comprises a delivery device, having a mouthpiece through which the powder is inhaled, a dose cassette comprising at least one drug cavity for each dose, comprising a dose to be delivered.

WO2010024759 relates to an inhaler. The inhaler comprises a base having at least one foil sealed cavity containing medicament. A separating element is attached to the foil for separating the foil from the cavity.

WO2010021589 relates to an inhaler in which an outlet cover is connected to a movable actuator portion located upstream of a sealed medicament-containing cavity. As the outlet cover is removed from the outlet, the actuator portion moves downstream of the cavity and a sealing foil becomes separated from the cavity.

One dose dry powder inhalers of the kinds above are provided with one metered dose that may be used for vaccinations, clinical trials or emergency healthcare, wherein the user is not a day-to-day user. The inhaler therefore goes to waste after just one use. These kinds of inhalers are, for economical reasons, kept to a minimum with regard to pieces and parts since their consumption is high and lifetime is low.

WO 2009/082341 and WO 2009/082343 disclose devices and methods for inhalation of medicament powders. In use the air flow that by-passes a powder-containing cavity generates an eddy in the cavity to deaggregate the powder and empty the powder from the cavity.

WO 2015/097034 discloses a single dose dry powder inhaler having a dry powder container near the air inlet and a strip that forms a part of the dry powder container and occludes the air outlet. The strip is removed prior to inhalation to expose the air outlet and the dry powder.

Nevertheless, there remains a need for a dry powder inhaler with improved emptying and deaggregation of the dry powder medicament from the inhaler.

SUMMARY

Accordingly, the present invention preferably seeks to mitigate, alleviate or eliminate one or more of the above-identified deficiencies in the art and disadvantages singly or in any combination and solves at least the above mentioned problems by providing in one aspect a dry powder inhaler comprising: a housing with a lower part to form at least one air inlet and at least one air outlet; at least one container in the lower part, the container having a cavity for a dry powder drug; and a chamber above the at least one container for deaggregation of the drug after emptying of the drug from the cavity; wherein upon inhalation by a user at the at least one air outlet, air flows from the at least one air inlet into and through the chamber to empty the drug from the cavity and convey the drug to the at least one outlet.

In another aspect there is provided a method of emptying a powder from an inhaler comprising: inhaling air through an inlet in a longitudinal direction towards an outlet on the inhaler; passing the flow of air into and through a chamber adjacent to a powder-containing cavity to empty the powder from the cavity in a direction opposing the longitudinal direction of the inhaled air; and conveying the mixture of air and powder out of the chamber to the outlet.

Further advantageous embodiments are disclosed in the appended and dependent patent claims.

BRIEF DESCRIPTION OF THE DRAWINGS

These and other aspects, features and advantages of which the invention is capable of will be apparent and elucidated from the following description of embodiments of the present invention, reference being made to the accompanying drawings, in which.

DETAILED DESCRIPTION

The following description focuses on two embodiments of the present invention applicable to a medicament inhaler, and in particular to a dry powder drug inhaler for a one dose administration. However, it will be appreciated that the invention is not limited to these applications but may be applied to many other inhalers having an inlet, an outlet, and a medicament container.

FIGS. 1 to 11 illustrate a dry powder drug inhaler 100 according to a first embodiment of the invention whilst FIGS. 12 to 22 illustrate a dry powder drug inhaler 200 according to a second embodiment of the invention. FIG. 23 illustrates the directional flow of air during use of the inhaler 200 although it will be understood the same air flow occurs during use of inhaler 100.

Figure 1:
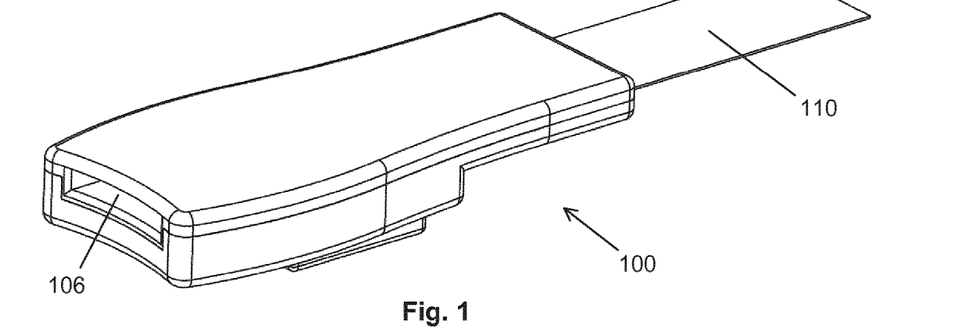
FIG. 1 is a perspective view from the inlet end of an inhaler according to a first embodiment of the present invention.
Figure 2:
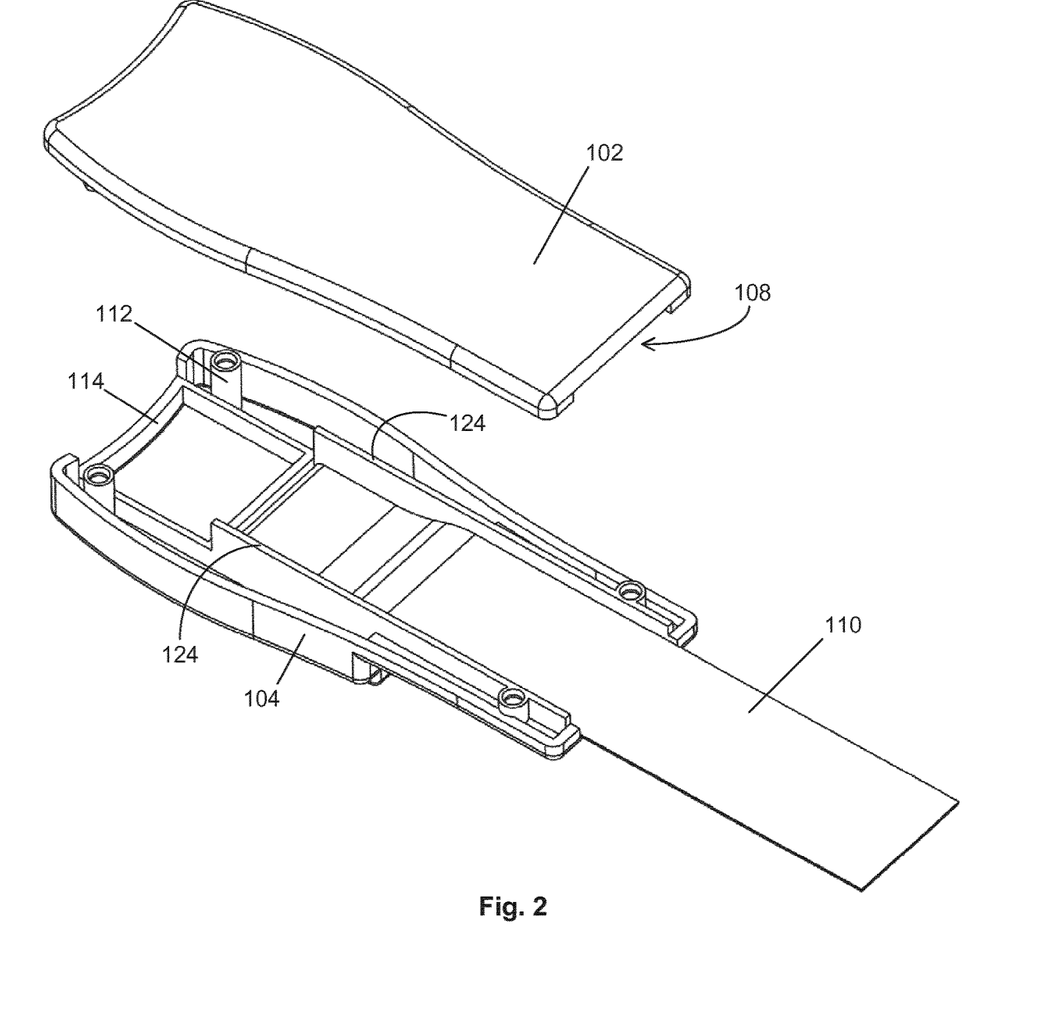
FIG. 2 is a separated perspective view from the outlet end of an inhaler according to a first embodiment of the present invention.

FIGS. 1 to 4 illustrate the major components and their relative arrangement in the dry powder drug inhaler 100. The dry powder drug inhaler 100 comprises a housing with an upper housing part 102 and a lower housing part 104 which are connected to each other via connecting elements 112. Although four connecting elements 112 on the lower housing part 104 are depicted in FIG. 2, any number of connecting elements may be utilized to join the upper and lowering housings together. Elements 112 may be provided as screw channels or male-female type fittings as known to the person skilled in the art. For example, one or more male fittings may be located on upper housing part 102 which snap fit into one or more corresponding female fittings located on the lower housing part 104.

The upper housing part 102 and the lower housing part 104 may be manufactured from any suitable material for example, injection moldable plastics such as thermoplastics.

When the upper housing part 102 and the lower housing part 104 are connected to each other they form an air inlet 106 and an air outlet 108. Inlet 106 is arranged at a first end of the inhaler 100 while the outlet 108 is arranged at an opposite second end of the inhaler 100. The number of inlets and outlets may be different from what is disclosed in FIGS. 1 to 11. The number of inlets may for example be adjusted in accordance with needs and specific inhaler design such that a number of smaller inlets, for reducing pressure fall over the inhaler, are arranged circumferentially of the inhaler 100. This is not shown. In a corresponding manner the number of air outlets may be adjusted in accordance with needs and specific inhaler design.

A wall 114 is located in the lower housing part 104 between the air inlet 106 and a chamber 122 that will be described below. Wall 114 is generally square-shaped with a slight curve in the side closest to air inlet 106 to conform with the shape of that end of the lower housing 104 as shown in FIG. 2. The wall in the lower housing part decreases the risk of the dry powder drug becoming trapped in the space between the air inlet 106 and the container 116 (described immediately below). The wall in the lower housing part also allows for a relatively simpler construction of the upper housing part 102.

Figure 3:
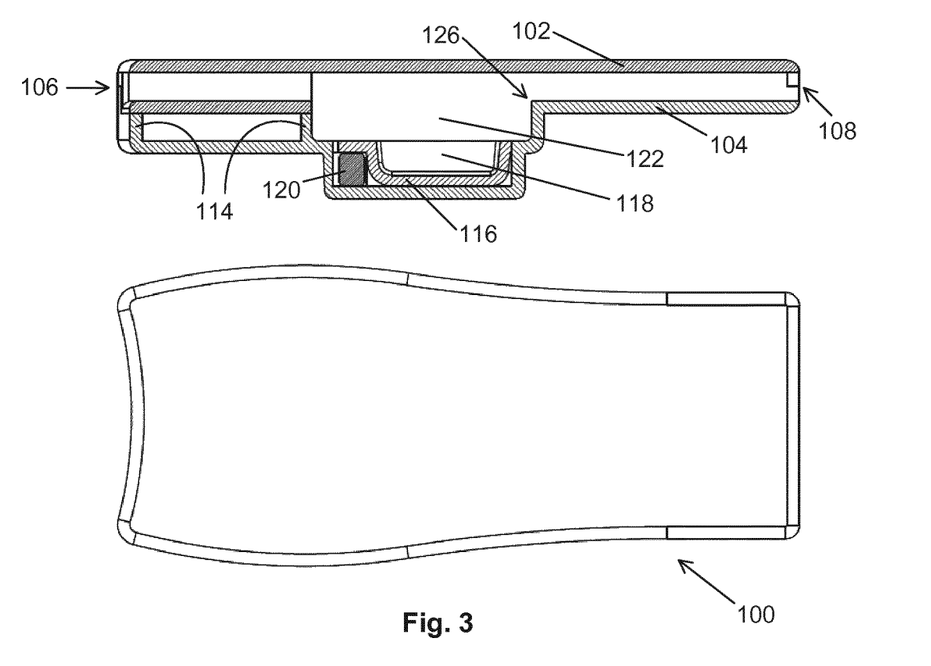
FIG. 3 shows a cross sectional side view and a top view along the longitudinal axis of an inhaler according to a first embodiment of the present invention.
Figure 4:
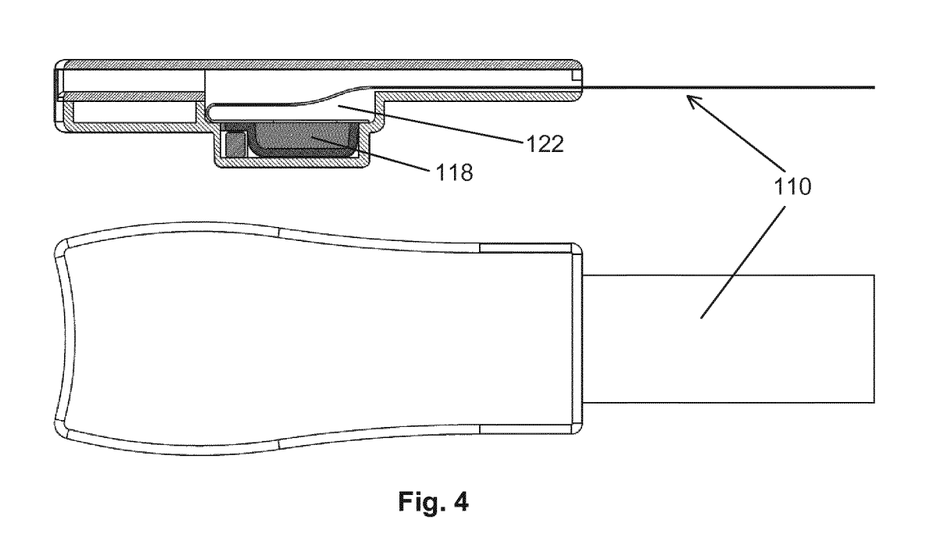
FIG. 4 shows another cross sectional side view and another top view along the longitudinal axis of an inhaler according to a first embodiment of the present invention.

The inhaler 100 further comprises at least one container 116 located in a central but low portion of the lower housing part 104 as shown in the cross-sectional side views of FIGS. 3 and 4. The container 116 has a cavity 118 for a dry powder drug. A desiccant tablet 120 is located under a lip of the container 116 and abuts one end of the container 116 for minimizing undesirable movement of the container 116 after its placement in the lower housing part 104. Desiccant tablet 120 may contain any suitable moisture absorbing agent(s) known to the person skilled in the art to help ensure that the dry powder drug retains its effectiveness. The container 116 may be formed integrally with lower housing part 104 during manufacture of the inhaler or may be inserted later into the lower housing as will be described with respect of FIGS. 5 to 11 below. Later insertion allows for pre-filling of the container with a drug prior to placement of the container 116 in the lower housing part 104.

A strip 110 is arranged on the inhaler 100 to cover the dry powder medicament in cavity 118 prior to use. As shown in FIG. 4, an internally located end portion of the strip 110 seals the powder-containing cavity 118 of container 116 before the remainder of the strip is looped back to extend longitudinally from the container 116 towards the outlet 108 and exterior of the inhaler 100. Prior to use the strip 110 is removed by pulling its externally located end portion away from the outlet 108 to reveal the drug in the container 116. The portion of the strip 110 located externally of the inhaler 100 may run along the outer surface of the lower or upper housing parts 102, 104 although this is not illustrated.

The strip 110 and the container 116 may be manufactured from any suitable material for holding and enclosing moisture sensitive drugs. One suitable material is aluminum foil optionally laminated with a plastic.

A chamber 122 is also present in lower housing part 104. The chamber 122 is located directly above the container 116 and below the longitudinal path of air flow between inlet 106 and outlet 108. The size and shape of the chamber 122 is not particularly limited. Preferably, the length and width of the chamber 122 are greater than the length and width of the container 116 in order that the chamber 122 completely covers, and extends beyond, the container 116. The volume of the chamber 122 is preferably greater than the volume of the container 116 and hence the volume of powder in the cavity.

Figure 9:
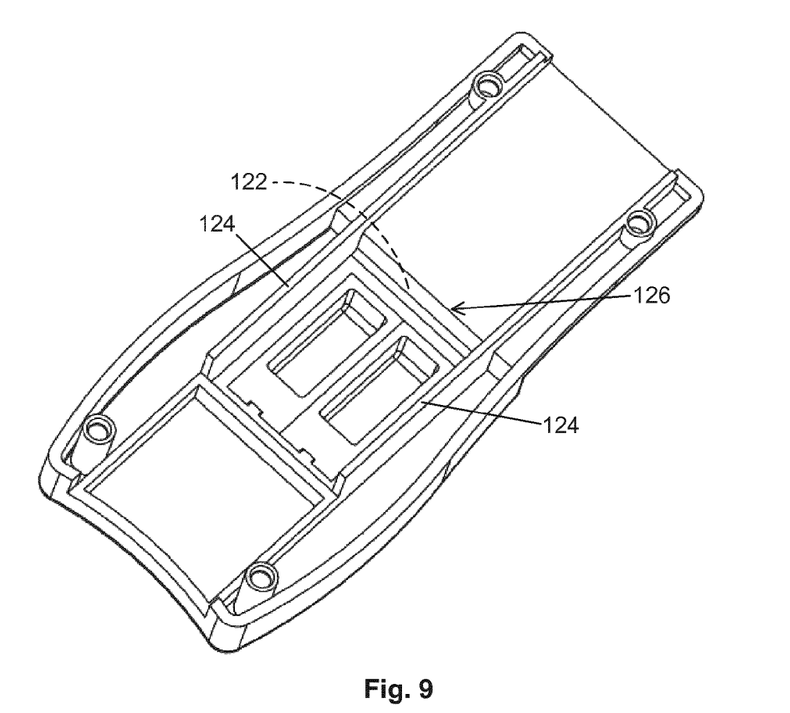
FIG. 9 is a perspective view from the inlet end of the lower housing of an inhaler according to a first embodiment of the present invention.
Figure 11:
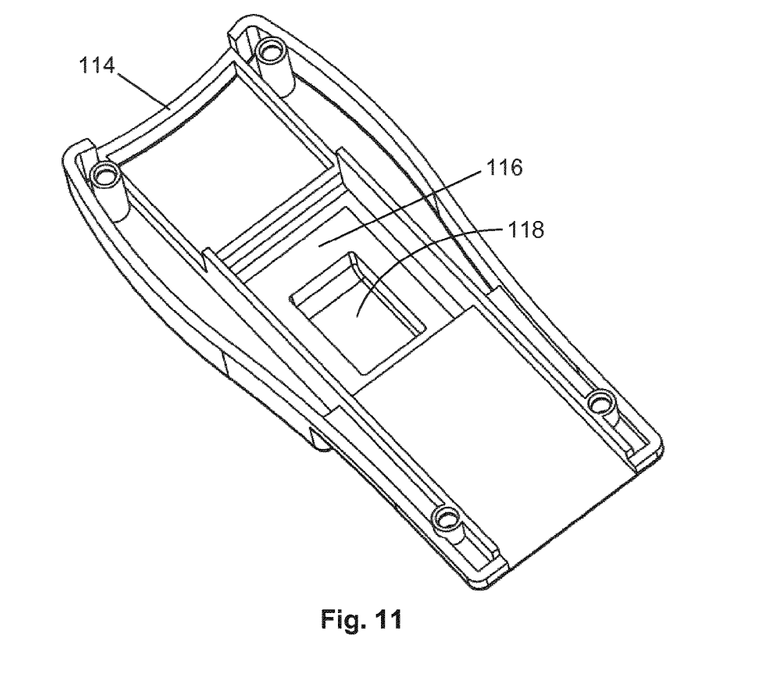
FIG. 11 is another perspective view from the outlet end of the lower housing of an inhaler according to a first embodiment of the present invention.
Figure 12:
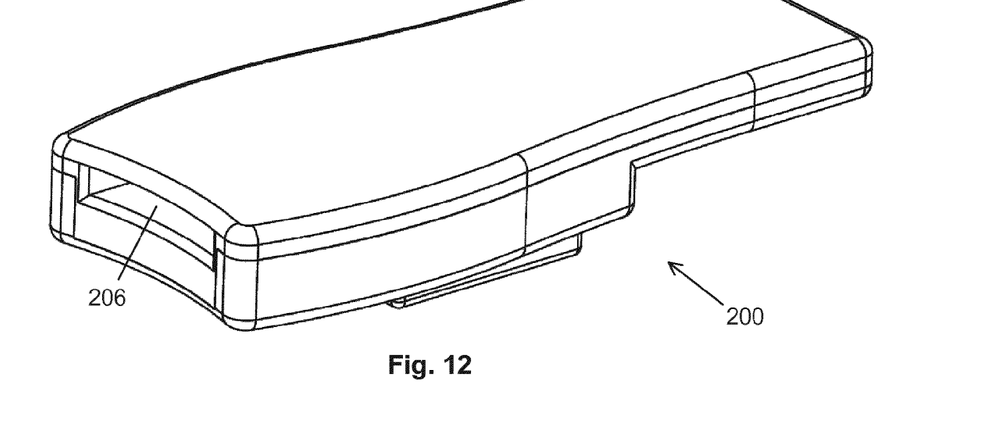
FIG. 12 is a perspective view from the inlet end of an inhaler according to a second embodiment of the present invention.
Figure 13:
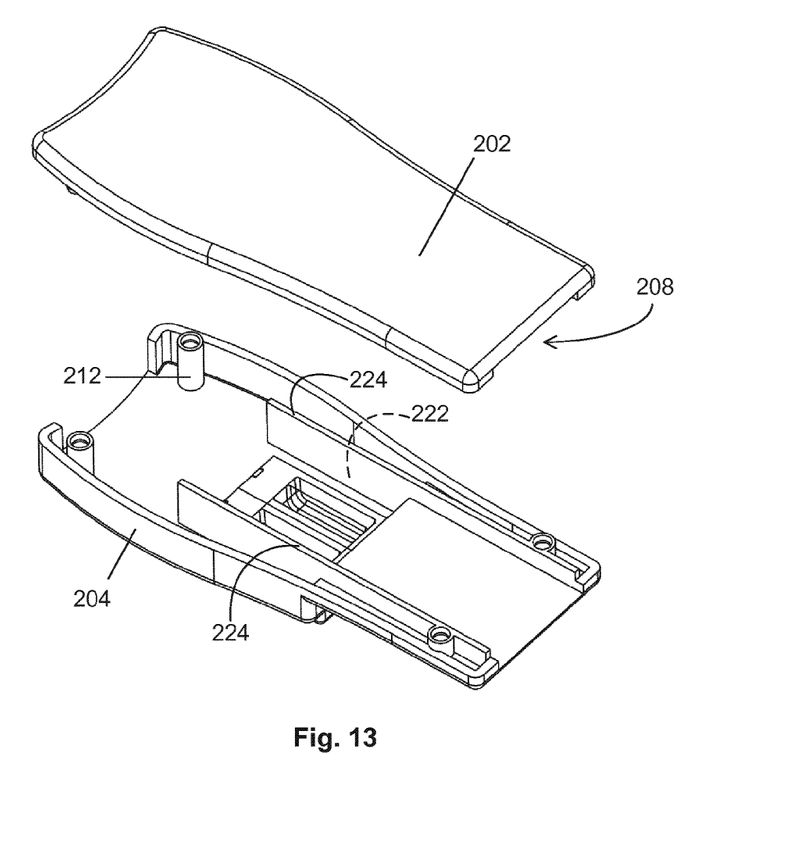
FIG. 13 is a separated perspective view from the outlet end of an inhaler according to a second embodiment of the present invention.

Horizontal ledges 124 and a horizontal edge 126 are located towards the periphery of the chamber 122. The ledges 124 extend longitudinally on opposing sides of the container 116, are parallel with each other, and form a right angle with edge 126 as shown in FIGS. 9 and 11. Ledges 124 may be inserted into lower housing part 104 or formed integrally with lower housing part 104. Edge 126 lies opposite wall 114 on opposing ends of the container 116. The edge 126 is formed during manufacture of the lower housing part 104. As will be described below in regard to use of the inhaler, chamber 122 facilitates formation of a strong whirl of air above the powder that leads to improved emptying of the powder from the container 116 and deaggregation of the powder in the chamber 122. Wall 114, ledges 124, and edge 126 further improve air turbulence and direct the air flow away from and even against the main flow entering from inlet 106. This result in an improved powder/air profile in the air stream exiting the inhaler 100 at the outlet 108 and increases the possibility of the powder entering an increased area/volume of the user's lungs.

Figure 5:
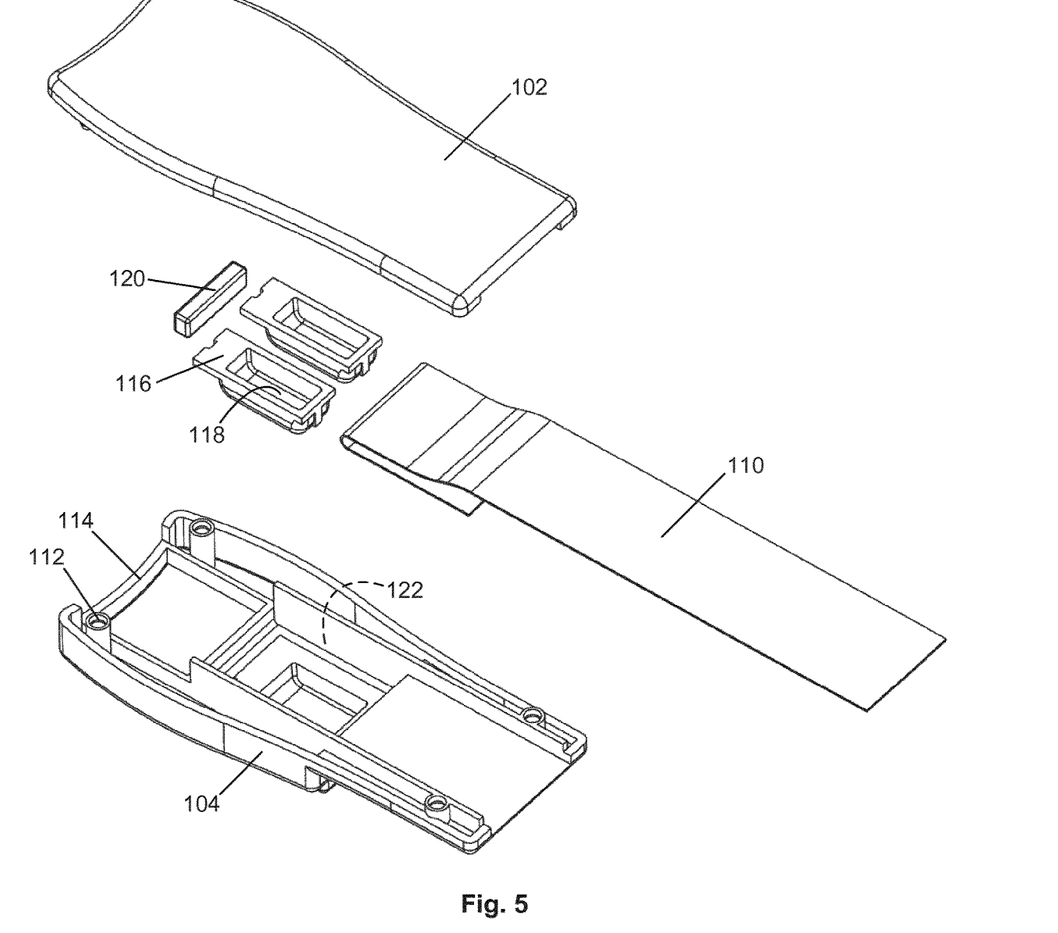
FIG. 5 is another separated perspective view from an outlet end of an inhaler according to a first embodiment of the present invention.
Figure 6:
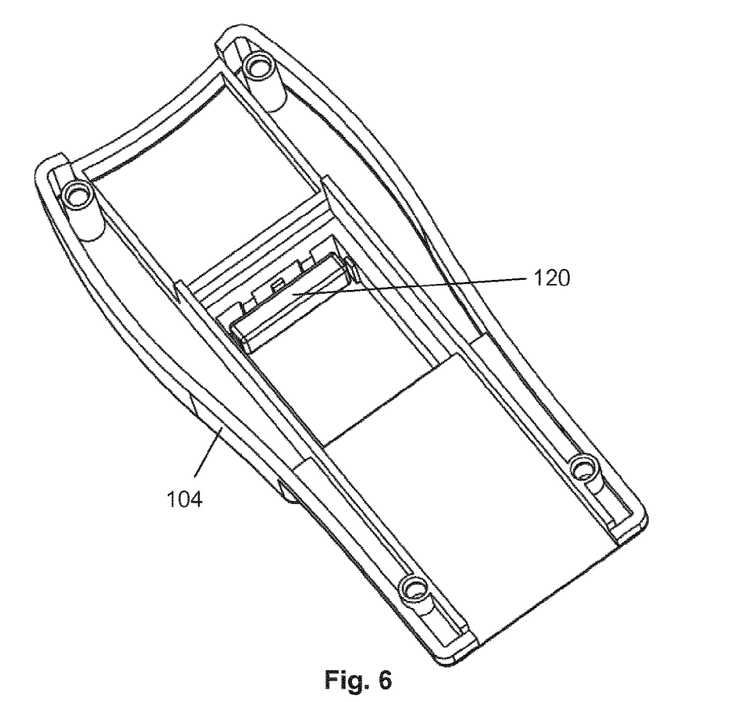
FIG. 6 is a perspective view from the outlet end of the lower housing of an inhaler according to a first embodiment of the present invention.
Figure 7:
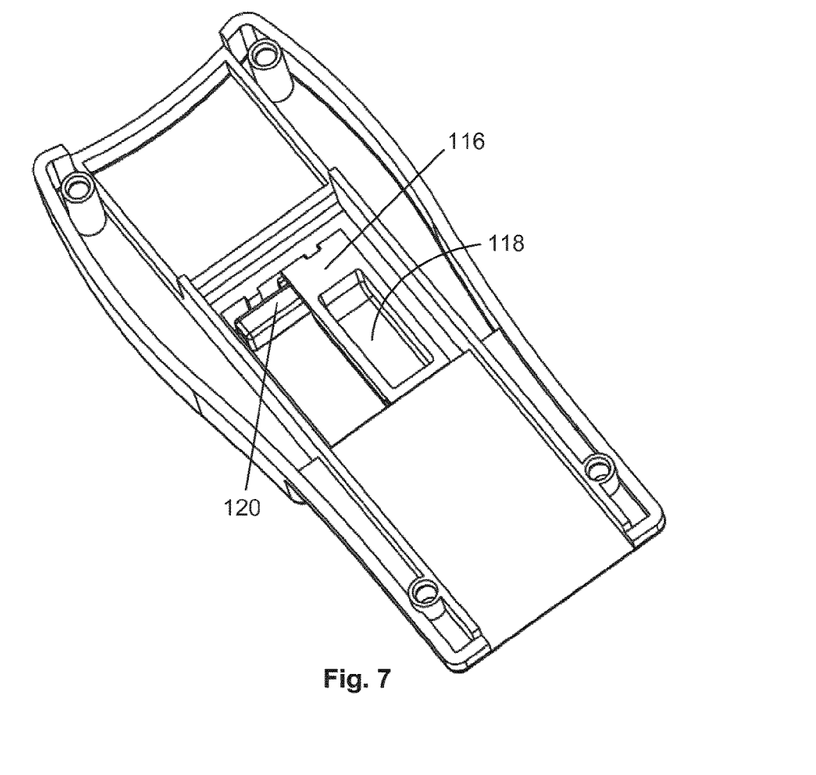
FIG. 7 is another perspective view from the outlet end of the lower housing of an inhaler according to a first embodiment of the present invention.
Figure 8:
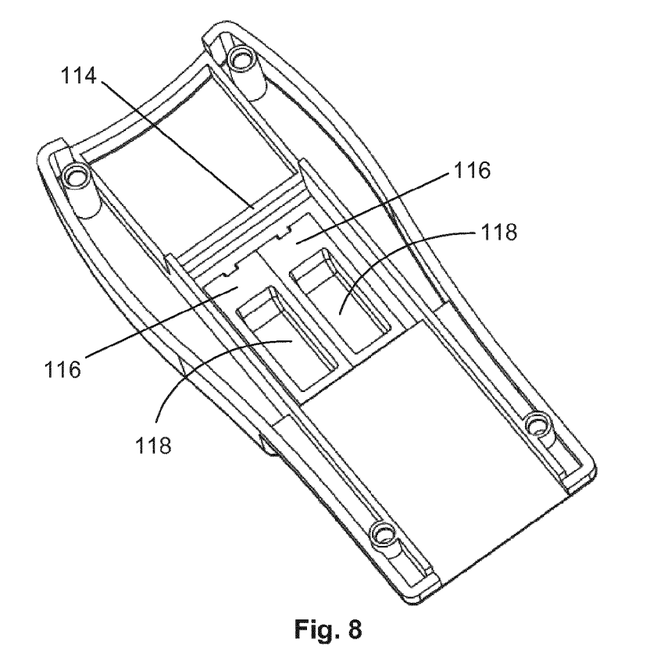
FIG. 8 is another perspective view from the outlet end of the lower housing of an inhaler according to a first embodiment of the present invention.
Figure 10:
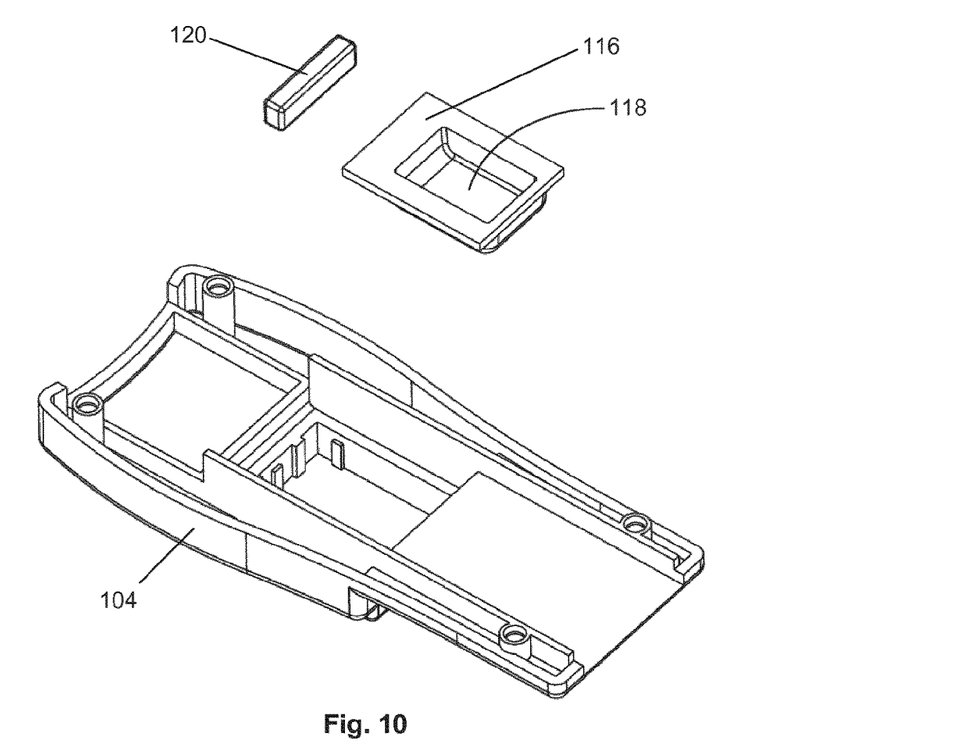
FIG. 10 is a separated perspective view from the outlet end of the lower housing of an inhaler according to a first embodiment of the present invention.

Inhaler 100 may have two containers 116 in the lower housing part 104 as illustrated in FIGS. 5, 8 and 9. Each container is preferably pre-filled with powder prior to its placement in the lower housing. It is not necessary that the containers 116 are identical in size as shown in FIG. 5. Provision of two (or more) containers 116 allows for use of the inhaler 100 with two (or more) different medicament powders. Varying the size of each container allows for administration of different dosage amounts. The inhaler 100 may have one powder-containing container 116 and one empty container 116 in order to achieve a specific whirl of air/powder mixture or more efficient emptying of a particular powder relative to emptying from a single larger container. An inhaler 100 with one container 116 as shown in FIGS. 10 and 11 allows for administration of a large dose of powder.

FIGS. 12 to 22 illustrate a dry powder drug inhaler 200 according to a second embodiment of the invention. The main difference between inhalers 100 and 200 is that inhaler 100 has a wall 114 in its lower housing part 104 whilst inhaler 200 has a wall 214 in its upper housing part 202 as will be described further below. Otherwise the inhaler 200 is similar in structure and function to inhaler 100 and thus only an abbreviated description of inhaler 200 is given below.

The dry powder drug inhaler 200 comprises an upper housing part 202 and a lower housing part 204 which are connected to each other via connecting elements 212. Any number of connecting elements may be utilized to join the upper and lowering housing parts together. Screw channels and male-female type fittings are examples of elements 212. The upper housing part 202 and the lower housing part 204 may be manufactured from injection moldable plastics such as thermoplastics.

Upon connection the upper housing part 202 and the lower housing part 204 form an air inlet 206 and an air outlet 208 at opposing ends of the inhaler 200. More than one inlet and/or outlet may be present and the number of inlets/outlets will depend on specific needs and inhaler design.

Figure 14:
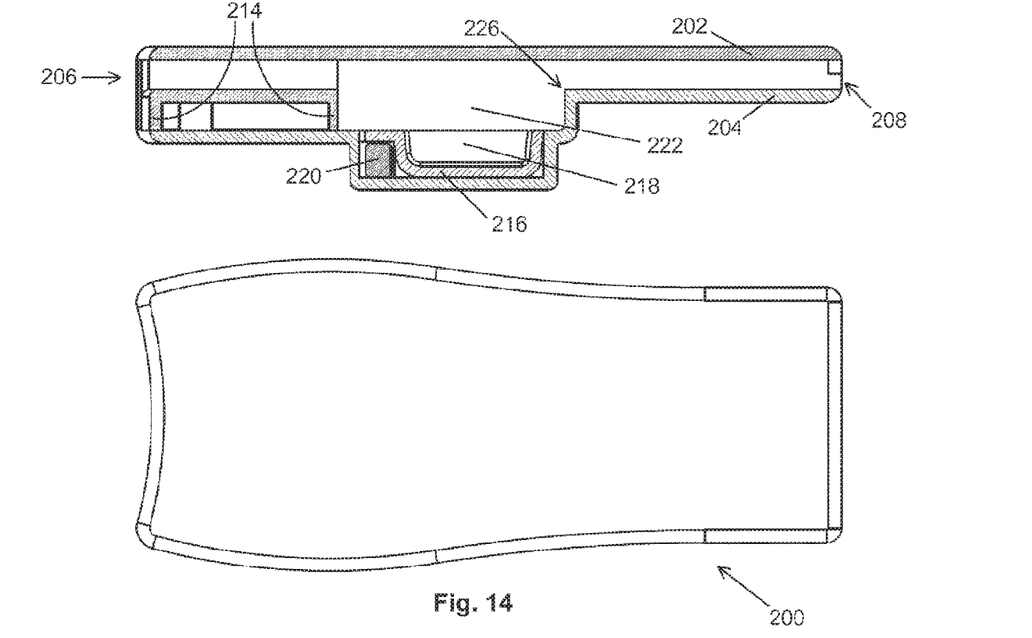
FIG. 14 shows a cross sectional side view and a top view along the longitudinal axis of an inhaler according to a second embodiment of the present invention.

A wall 214 is located in the upper housing part 202 between chamber 222 and the air inlet 206 as shown in FIG. 14. The location of the wall in the upper housing allows for easier placement of at least one container 216 in the lower housing part 204 during assembly of the inhaler 200.

Figure 15:
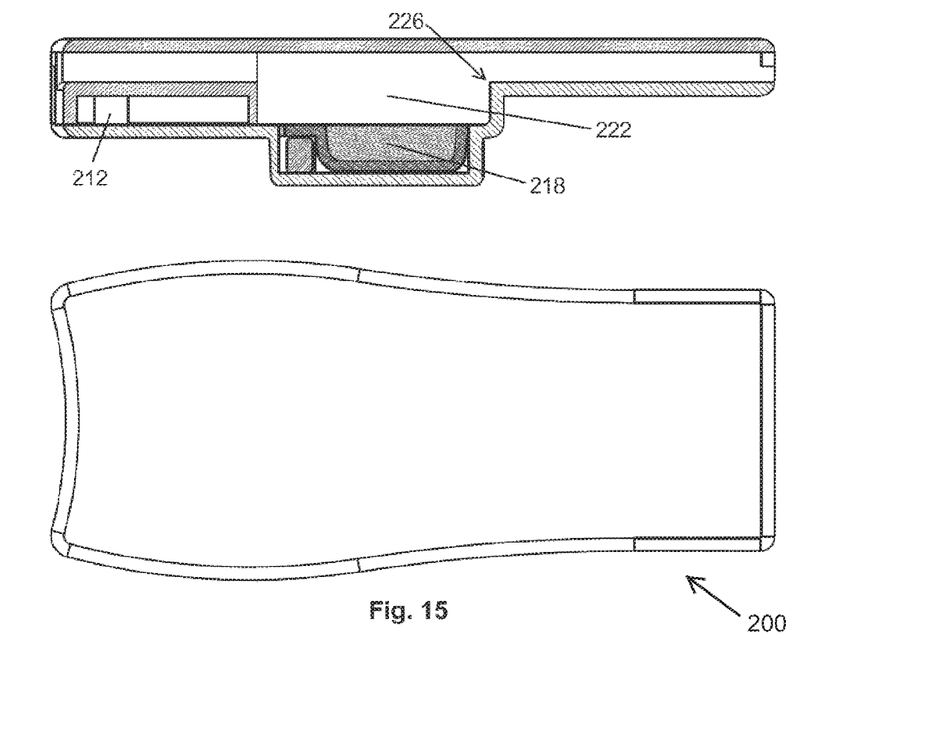
FIG. 15 shows another cross sectional side view and another top view along the longitudinal axis of an inhaler according to a second embodiment of the present invention.

The inhaler 200 further comprises at least one container 216 in the lower housing part 204 as shown in the cross-sectional side views of FIGS. 14 and 15. The container 216 has a cavity 218 for receiving a dry powder drug. A desiccant tablet 220 for absorbing moisture abuts one end of the container 216 thereby minimizing movement of the container 216 and avoiding loss of powder from the cavity.

No strip corresponding to strip 110 of inhaler 100 is depicted in FIGS. 12 to 22 although it will be understood that inhaler 200 may also have a strip analogous to strip 110. The strip and the container 216 may be manufactured from aluminum foil optionally laminated with a plastic.

Figure 20:
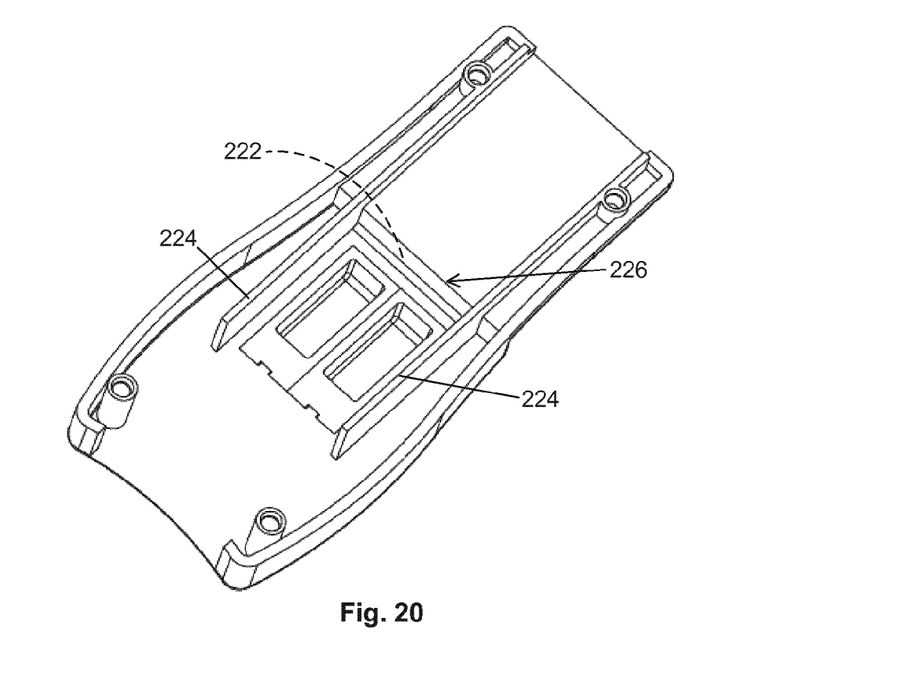
FIG. 20 is a perspective view from the inlet end of the lower housing of an inhaler according to a second embodiment of the present invention.

A chamber 222 is located directly above the container 216 and below the longitudinal path of air flow between inlet 206 and outlet 208. It is preferred the length and width of the chamber 222 are greater than the length and width of the container 216 in order that the chamber 222 completely covers the container 216. The volume of the chamber 222 is preferably greater than the volume of the container 216. Horizontal ledges 224 and a horizontal edge 226 are located at right angles to each other on the periphery of the chamber 222 as illustrated in FIG. 20. Chamber 222, inner wall 214, ledges 224, and edge 226 allow for improved emptying of the powder from the container 216 and deaggregation of the powder in the chamber 222 through formation of a strong whirl of air as described below in regard to use of the inhaler.

Figure 16:
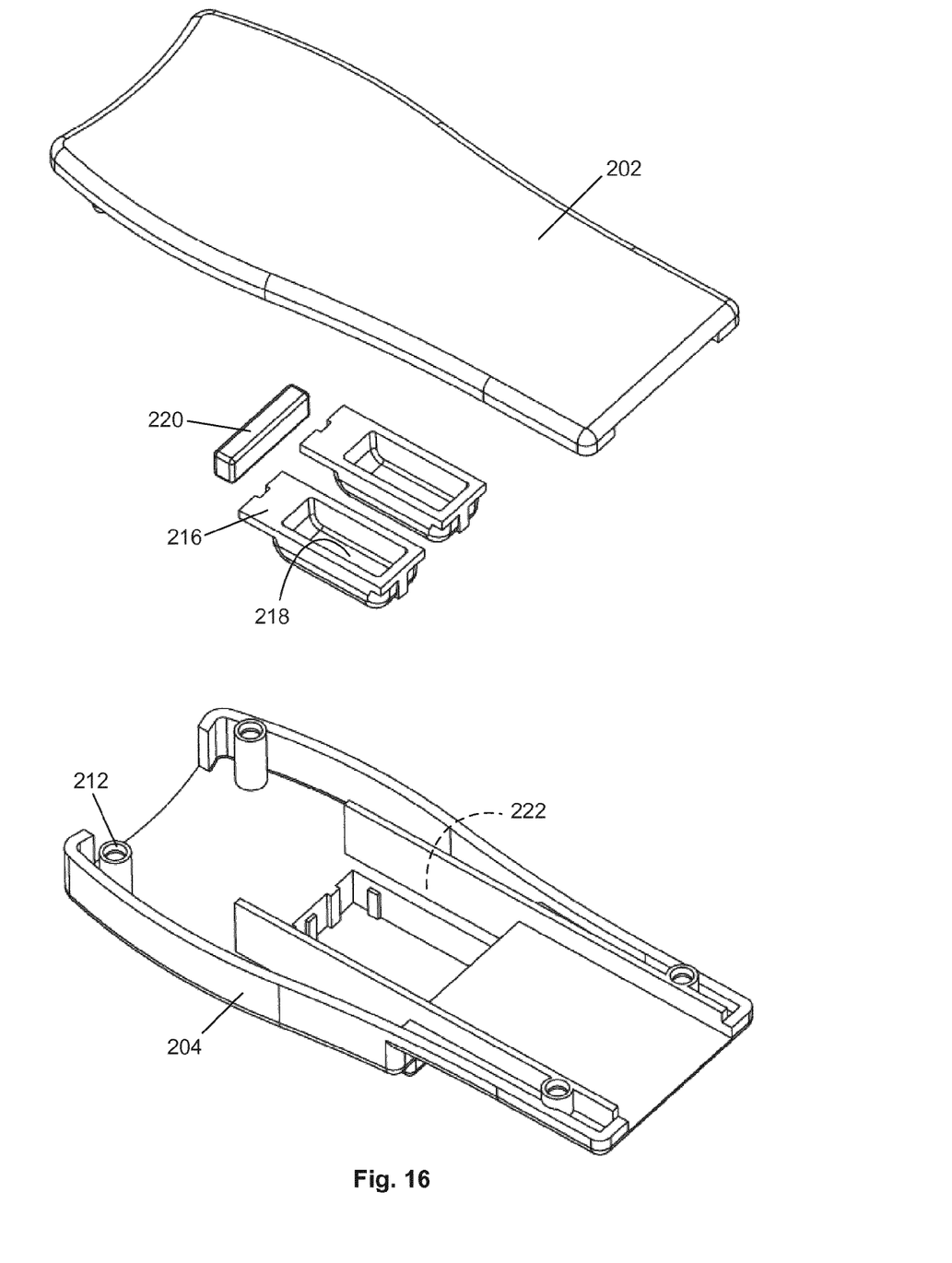
FIG. 16 is another separated perspective view from the outlet end of an inhaler according to a second embodiment of the present invention.
Figure 17:
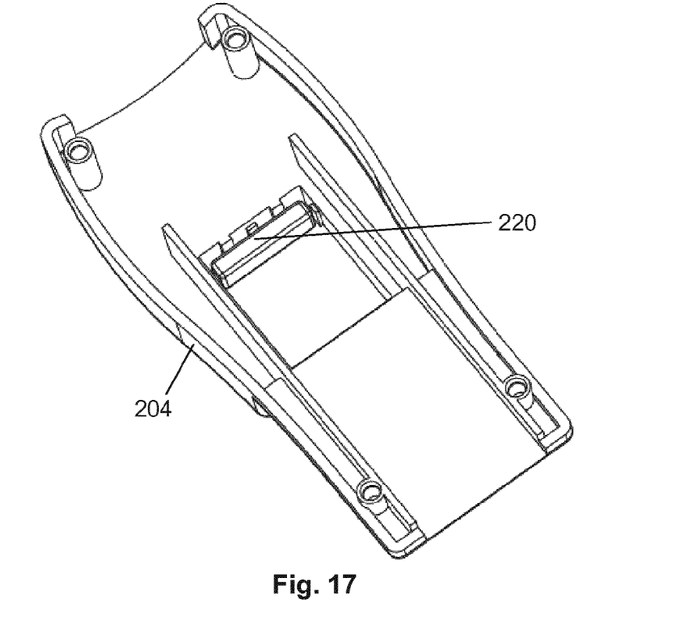
FIG. 17 is a perspective view from the outlet end of the lower housing of an inhaler according to a second embodiment of the present invention.
Figure 18:
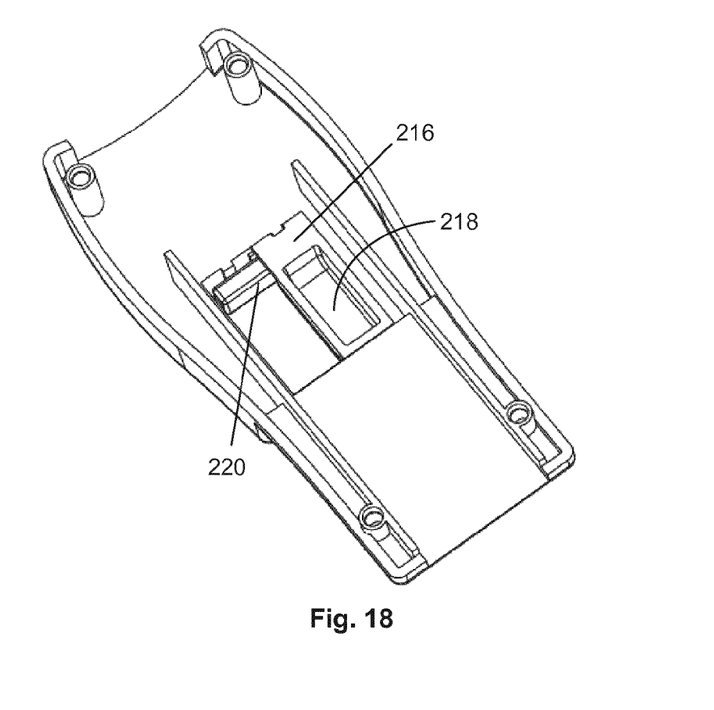
FIG. 18 is another perspective view from the outlet end of the lower housing of an inhaler according to a second embodiment of the present invention.
Figure 19:
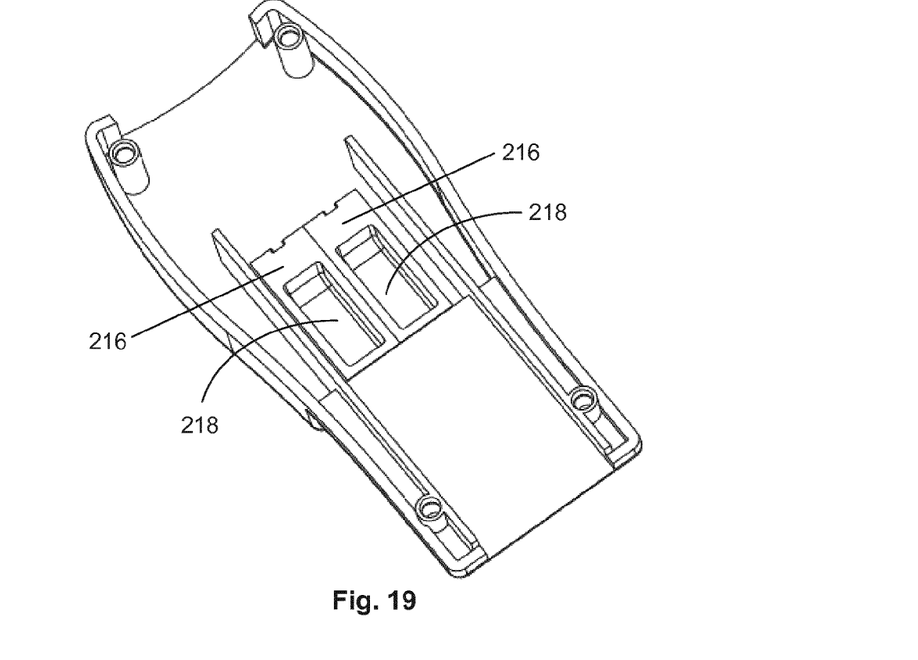
FIG. 19 is another perspective view from the outlet end of the lower housing of an inhaler according to a second embodiment of the present invention.
Figure 21:
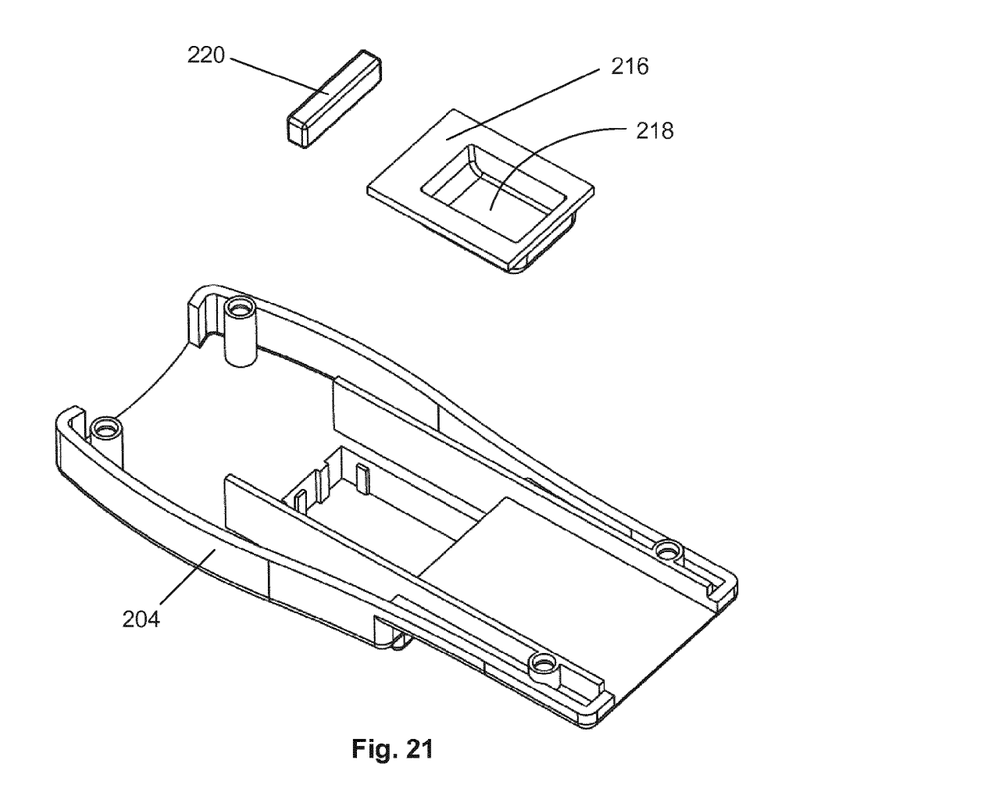
FIG. 21 is a separated perspective view from the outlet end of the lower housing of an inhaler according to a second embodiment of the present invention.
Figure 22:
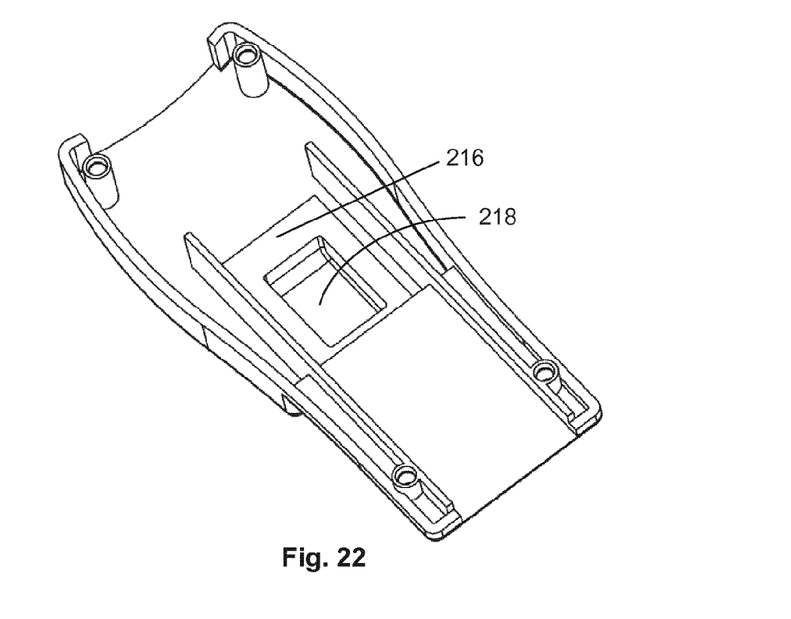
FIG. 22 is another perspective view from the outlet end of the lower housing of an inhaler according to a second embodiment of the present invention.
Figure 23:
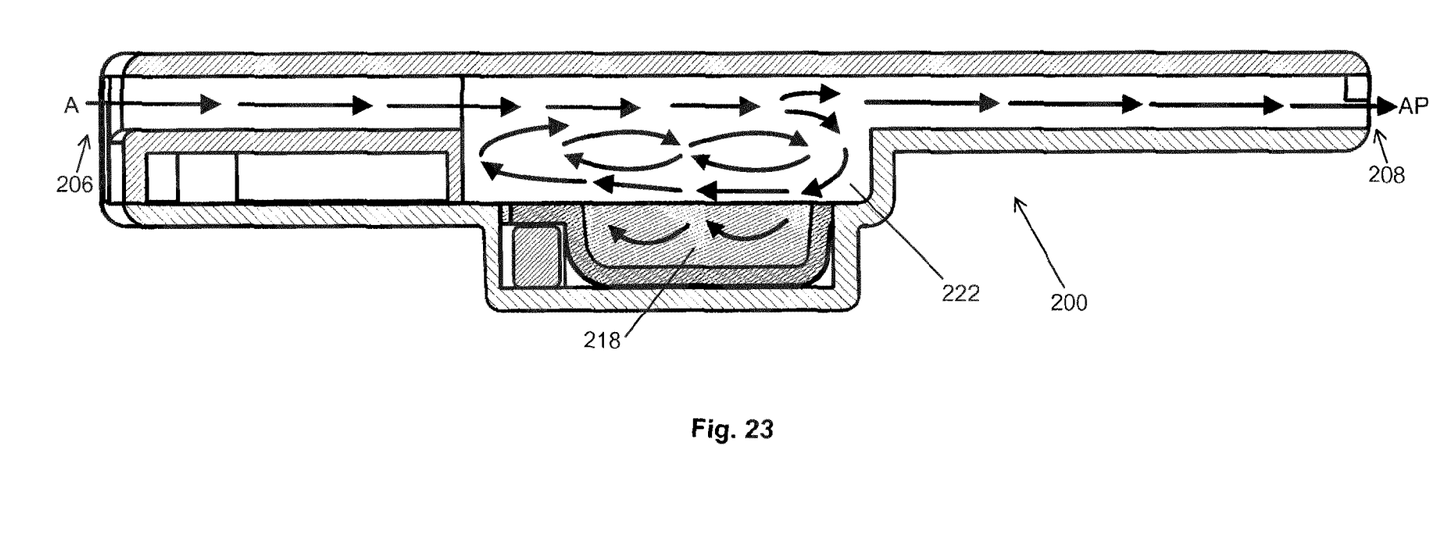
FIG. 23 shows the direction of air flow (A) during use of the inhaler in the cross sectional side view of FIG. 15.

Inhaler 200 may have two containers 216 as illustrated in FIGS. 16, 19 and 20 or one container 216 as shown in FIGS. 18, 21 and 22. The containers 216 may have different sizes and are preferably pre-filled with powder prior to their placement in the lower housing part. The number of containers and their size will depend on the number, type and quantity of medicament powder(s) to be administered.

The inhaler 100, 200 is generally used as follows with reference to FIG. 23. A user removes the strip 110 to expose the powder in the at least one container 116, 216. The user then brings the outlet 108, 208 to his/her mouth and inhales such that air (A) begins to flow through the inlet 106, 206 along a longitudinal path extending towards the outlet 108, 208. The flow of air (A) is represented by the direction of the arrows through the inhaler 200 in FIG. 23. As the air flow passes the chamber 122, 222, the air flow enters and forms a strong whirl of air in the chamber 122, 222 that empties the powder from the cavity 118, 218 in the container 116, 216. The air flow mechanics in the chamber 122, 222 improve deaggregation of the powder by allowing for a whirl of air that empties the cavity from right to left of the inhaler 100, 200 i.e. against the main air flow (A) which travels from left to right of the inhaler 100, 200 as illustrated by the arrows in FIG. 23. The powder disperses into the whirl of air in the chamber 122, 222 before being conveyed in the air flow upwards and further along the longitudinal path towards outlet 108, 208. The air flow/powder mixture (AP) then exits the inhaler 100, 200 into the respiratory tract of the user.

Although, the present invention has been described above with reference to specific embodiments, it is not intended to be limited to the specific form set forth herein. Rather, the invention is limited only by the accompanying claims.

In the claims, the term "comprises/comprising" does not exclude the presence of other elements or steps. Furthermore, although individually listed, a plurality of means, elements or method steps may be implemented by e.g. a single unit or processor. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "first", "second" etc do not preclude a plurality. Reference signs in the claims are provided merely as a clarifying example and shall not be construed as limiting the scope of the claims in any way.

The invention claimed is:

1. A dry powder inhaler, comprising:
   a housing having a lower housing part defining at least one air inlet, at least one air outlet, and a first direction extending between the at least one air inlet and the at least one air outlet;
   at least one container disposed in the lower housing part, the at least one container having a cavity configured for a dry powder drug;
   a chamber present in the lower housing part and disposed above the at least one container in a second direction extending perpendicular to the first direction, the chamber configured for deaggregation of the dry powder drug after emptying of the dry powder drug from the cavity;
   wherein upon inhalation by a user at the at least one air outlet, air flows from the at least one air inlet into and through the chamber to empty the dry powder drug from the cavity and convey the dry powder drug to the at least one outlet;
   wherein a length of the chamber in the first direction is greater than a total length spanned by the at least one container in the first direction;
   wherein a width of the chamber in a third direction is greater than a total width spanned by the at least one container in the third direction;
   wherein the third direction extends perpendicular to the first direction and perpendicular to the second direction;
   wherein the housing comprises an upper housing part connectable with the lower housing part to define the at least one air inlet and the at least one air outlet;
   wherein the chamber is disposed exclusively above the cavity of the at least one container in the second direction; and
   the air is flowable into the cavity exclusively via the chamber.

2. The dry powder inhaler according to claim 1, wherein a volume of the chamber is greater than a volume of the at least one container.

3. The dry powder inhaler according to claim 1, wherein:
   the lower housing part includes at least two horizontal ledges that protrude from the lower housing part and that extend in the first direction on opposite sides of the at least one container; and
   the lower housing part has at least one horizontal edge extending between the at least two horizontal ledges at a periphery of the chamber.

4. The dry powder inhaler according to claim 1, further comprising a strip configured to seal the cavity prior to use, wherein the strip extends longitudinally away from the at least one container towards the at least one air outlet and an exterior of the housing.

5. The dry powder inhaler according to claim 2, wherein the lower housing part includes a wall protruding toward the upper housing part between the at least one container and the at least one air inlet, and wherein the wall at least partially defines the chamber.

6. The dry powder inhaler according to claim 5, wherein the wall is square-shaped and includes a curve on a side adjacent to the at least one air inlet.

7. The dry powder inhaler according to claim 2, wherein the upper housing part includes a wall protruding toward the lower housing part between the at least one container and the at least one air inlet, and wherein the wall at least partially defines the chamber.

8. The dry powder inhaler according to claim 1, further comprising a desiccant tablet abutting the at least one container.

9. The dry powder inhaler according to claim 8, wherein:
   the at least one container includes (i) a sidewall facing in the first direction and at least partially defining the cavity, and (ii) a lip protruding from the sidewall in the first direction; and
   the desiccant tablet is disposed under the lip of the at least one container in abutment with the sidewall of the at least one container and a sidewall of the lower housing part facing in the first direction restricting movement of the at least one container within the housing.

10. The dry powder inhaler according to claim 1, further comprising at least one connector structured and arranged to connect the lower housing part and the upper housing part.

11. The dry powder inhaler according to claim 1, wherein:
   the lower housing part includes (i) an upper portion, (ii) a lower portion, and (iii) an intermediate portion disposed between the upper portion and the lower portion relative to the second direction;
   the upper portion of the lower housing part at least partially defines a longitudinal air flow path extending between the at least one air inlet and the at least one air outlet in the first direction;
   the intermediate portion of the lower housing part protrudes from the upper portion in the second direction and at least partially defines the chamber;
   the lower portion of the lower housing part protrudes from the intermediate portion in the second direction and defines a container receptacle, the chamber disposed between the container receptacle and the air flow path;
   the intermediate portion and the lower portion each define a substantially U-shaped profile in a cross-section perpendicular to the third direction; and the at least one container is disposed within the container receptacle.

12. The dry powder inhaler according to claim 11, wherein a desiccant tablet is disposed in a corner region of the container receptacle and separates a sidewall of the at least one container and a sidewall of the lower housing part that at least partially delimits the container receptacle.

13. The dry powder inhaler according to claim 11, wherein the container receptacle opens into the chamber through a bottom surface of the intermediate portion that faces in the second direction and at least partially defines the chamber.

14. The dry powder inhaler according to claim 1, wherein:
the at least one container includes a notch protruding into the at least one container;
a sidewall of the lower housing part includes a protrusion structured complimentary to the notch of the at least one container; and
the protrusion is engaged with the notch.

15. The dry powder inhaler according to claim 1, wherein:
the lower housing part includes a plurality of female connecting structures disposed around a periphery of the lower housing part and protruding toward the upper housing part;
the upper housing part includes a plurality of male connecting structures structured and arranged in a complimentary manner to the plurality of female connecting structures; and
the upper housing part and the lower housing part are connectable via engaging the plurality of male connecting structures and the plurality of female connecting structures in a snap fit manner.

16. The dry powder inhaler according to claim 1, further comprising a single longitudinal air flow path extending between the at least one air inlet and the at least one air outlet, wherein the chamber is disposed exclusively between the cavity of the at least one container and the longitudinal air flow path relative to the second direction.

17. A method of emptying a powder from an inhaler, comprising:
inhaling air through an inlet of a housing of the inhaler in a first direction towards an outlet of the housing;
passing a flow of the air into and through a chamber disposed adjacent to a powder-containing cavity of at least one container to empty the powder from the cavity in a direction opposing the first direction, the chamber present in a lower housing part of the housing and disposed above the cavity in a second direction extending perpendicular to the first direction, the chamber having a length in the first direction and a width in a third direction that are greater than a total length in the first direction and a total width in the third direction spanned by the at least one container, the third direction extending perpendicular to the first direction and perpendicular to the second direction;

conveying a mixture of the air and the powder out of the chamber to the outlet;

wherein the housing comprises an upper housing part connectable with the lower housing part to define the inlet and the outlet;

wherein the chamber is disposed exclusively above the cavity of the at least one container in the second direction; and the air is flowable into the cavity exclusively via the chamber.

18. A dry powder inhaler, comprising:

a housing including a lower housing part and an upper housing part connected to the lower housing part, the upper housing part and lower housing part both defining at least one air inlet, at least one air outlet, and a longitudinal air flow path extending between the at least one air inlet and the at least one air outlet;

the lower housing part including (i) an upper portion at least partially defining the air flow path, (ii) a lower portion defining a container receptacle, and (iii) an intermediate portion disposed between and connecting the upper portion and the lower portion;

at least one container disposed in the container receptacle of the lower housing part, the at least one container defining a cavity configured to releasably retain a dry powder drug;

the intermediate portion of the lower housing part at least partially defining a chamber, the chamber disposed (i) exclusively above the cavity of the at least one container and (ii) exclusively below the longitudinal air flow path relative to the upper housing part, the chamber structured and arranged to facilitate deaggregation of the dry powder drug after emptying of the dry powder drug from the cavity; and wherein air is flowable into and out of the cavity exclusively via the chamber such that, upon inhalation by a user at the at least one air outlet, the air flows from the at least one air inlet into and through the chamber to empty the dry powder drug from the cavity and convey the dry powder drug to the at least one air outlet.

* * * * *